United States Patent [19]

McGill

[11] 4,298,546

[45] Nov. 3, 1981

[54] ISOMERIZATION OF 2-METHYL-3-BUTENENITRILE

[75] Inventor: Robert N. McGill, Orange, Tex.

[73] Assignee: E. I. Du Pont de Nemours and Company, Wilmington, Del.

[21] Appl. No.: 175,398

[22] Filed: Aug. 5, 1980

[51] Int. Cl.³ .......................................... C07C 121/30
[52] U.S. Cl. .................................................. 260/465.9
[58] Field of Search ...................................... 260/465.9

[56]     References Cited
     U.S. PATENT DOCUMENTS 3,536,748 10/1970 Drinkard, Jr. et al. .......... 260/465.9
3,542,847 11/1970 Drinkard, Jr. et al. .......... 260/465.9
3,676,481  7/1972 Chia ................................. 260/465.9
3,852,328 12/1974 Chia et al. ....................... 260/465.9
3,852,329 12/1974 Tomlinson ....................... 260/465.9
3,853,948 12/1974 Drinkard, Jr. et al. .......... 260/465.9

Primary Examiner—Joseph Paul Brust

[57]     ABSTRACT

The selectivity of isomerization of 2-methyl-3-butenenitrile to linear unconjugated pentenenitriles (e.g., 3-pentenenitrile) is increased by conducting the isomerization reaction in the presence of butadiene. The linear penetenenitrile products are useful as intermediates in the preparation of adiponitrile.

3 Claims, No Drawings

ISOMERIZATION OF 2-METHYL-3-BUTENENITRILE

BACKGROUND OF THE INVENTION

1. Field of the Invention

This invention is directed to the isomerization of 2-methyl-3-butenenitrile to linear pentenenitriles and more particularly to the isomerization of 2-methyl-3-butenenitrile to 3-pentenenitriles with improved selectivity using a zero-valent nickel complex as a catalyst for the isomerization.

2. Description of the Prior Art

U.S. Pat. No. 3,536,748 issued on Oct. 27, 1970 and assigned to E. I. du Pont de Nemours and Company discloses a process for the catalytic isomerization of 2-methyl-3-butenenitrile to linear pentenenitrile such as 3-pentenenitrile using a zero-valent nickel catalyst. Improvements and/or modifications to the aforesaid isomerization are also disclosed. U.S. Pat. No. 3,853,948 issued on Dec. 10, 1974 and assigned to E. I. du Pont de Nemours and Company, discloses an improved isomerization using an excess of neutral ligand over that required to form the zero-valent nickel complex. U.S. Pat. No. 3,676,481 issued on July 11, 1972 and assigned to E. I. du Pont de Nemours and Company describes the use of certain metal salts and/or tri(hydrocarbon) boron compounds as promoters for the zero-valent nickel catalysts used in the isomerization reaction. U.S. Pat. No. 3,852,329 issued on Dec. 3, 1974 and assigned to E. I. du Pont de Nemours and Company discloses a method for improving the yield of 3-pentenenitrile from the isomerization of 2-methyl-3-butenenitrile using a zero-valent nickel catalyst by initially contacting the potential reactants with a zeolite molecular sieve prior to the isomerization. Certain $\pi$-allyl nickel complexes having ligands whose cone angles lie in the range of 130°–170° C. are disclosed as preferred catalysts for the isomerization reaction in U.S. Pat. No. 3,852,328 issued on Dec. 3, 1974 and assigned to E. I. du Pont de Nemours and Company.

SUMMARY OF THE INVENTION

The present invention involves an improvement in a process for the isomerization of 2-methyl-3-butenenitrile to linear nitriles, for example, 3-pentenenitriles using a zero-valent nickel compound as a catalyst wherein the isomerization is conducted in the liquid phase in the presence of butadiene. This use of butadiene results in an improvement in the selectivity of the isomerization and in many cases, also results in improved catalyst utility and increased reaction rate.

DESCRIPTION OF THE PREFERRED EMBODIMENTS

The isomerization may be conducted under a wide range of conditions from below to above atmospheric pressure and at a temperature in the range 10°–200° C. Preferably and usually, the isomerization is conducted at or near atmospheric pressure and at a temperature in the range 100°–150° C. The isomerization can be conducted intermittently as in conventional batch operations but, preferably, is conducted continuously. The reaction pressure is chosen so that the reaction is conducted in the liquid phase. The reaction is conducted in any equipment which is suitably resistant to the reactants involved, e.g., stainless steel, carbon steel, Monel, etc. The reaction time will depend upon the relative amount of reactants and the degree of conversion desired, but can vary from a few seconds to many hours. The time required for a commercially acceptable level of conversion is dependent to a great extent upon the temperature of the reaction.

Solvents, diluents or other hydrocarbons that are nondestructive to the catalysts or reactants can be present. Suitable solvents include, for example, aliphatic or aromatic hydrocarbons (hexane, cyclohexane, benzene), ethers, (diethyl ethers, and dioxanes) esters, (ethyl acetate). It is preferred to conduct the present process in the absence of any added diluent or solvent. The zero-valent nickel catalysts which are employed in the isomerization tend to deactivate on contact with oxygen and therefore an inert atmosphere, e.g., nitrogen may be employed over the reaction surface. Air can be tolerated if the oxidative deactivation of the catalyst is not a serious penalty under the conditions of a particular reaction.

Catalysts which are employed in the isomerization, are nickel complexes of the general formula $Ni(PXYZ)_4$ wherein nickel is complexed with the neutral ligand PXYZ and wherein X is OR and Y and Z are selected from the class consisting of R and OR, R being selected from the class consisting of alkyl and aryl groups having up to 18 carbon atoms. If desired, any of X, Y and Z may be cojoined. Examples of divalent cojoined Y and Z are tetramethylene, pentamethylene, and ethylenedioxy groups. The ethylenedioxy group is an example of divalent cojoined X and Y or Z. It is believed that in these nickel compounds (complexes) at least some of the nickel is present in the zero-valent state. The preferred catalysts are the zero-valent nickel complexes in which the neutral ligands P(XYZ) are the aryl phosphites, such as triphenyl phosphite, tris(p-chlorophenyl)phosphite, tris(p-methoxyphenyl)phosphite, tris(p-tolyl)phosphite and mixed tris(m- and p-tolyl)phosphite. Under some of the reaction conditions of the present invention, one or more of the ligands may become dissociated from the nickel. In this specification, however, specific mention of one of the $Ni(PXYZ)_4$ compounds as a catalyst refers to the compound added to the reaction mixture.

In a preferred embodiment an excess of the ligand over that required to form the nickel complex is used in the isomerization. The neutral ligands used in excess are defined as in the nickel complexes above and comprise in general phosphites, phosphonites and phosphinites. Typical illustrations include compounds of the formulae

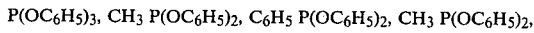

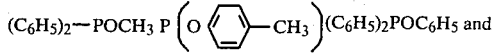

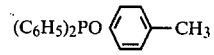

The preferred excess ligands are the aryl phosphites. Generally, the excess ligand is present in at least a 1 molar and preferably a 5–15 molar excess based on the nickel complex present. The excess ligand used may be the same or different from the ligand attached to nickel in the intermediate nickel compound and mixtures of different ligands can be used. Other ligands which are useful as catalysts are sigma-pi bonding ligands (PXYZ) in which X is OR, Y and Z are R or OR and R is an alkyl or aryl radical having up to 18 carbon atoms wherein for the π-allyl nickel compound the R radicals of a given PXYZ ligand are so chosen that the ligand has a cone angle in the range of 130°–170°. Suitable phosphorus ligands for the zero-valent nickel compounds of the type Ni(PXYZ)$_4$ include such phosphorus compounds as triphenyl phosphite, tri-m-tolyl phosphite, tri-p-tolyl phosphite, tri-(m & p-tolyl)phosphite, tri-(m & p-methoxyphenyl)phosphite and mixtures thereof. Suitable ligands of the type PXYZ for the π-allyl nickel compounds include tri-o-tolyl phosphite, tri-(2,5-xylyl) phosphite, tri-(2,4-xylyl)phosphite, tri-(o-phenylphenyl)phosphite, di-o-tolyl phenyl phosphonite, diphenyl phenyl phosphonite and phenyl diphenyl phosphinite.

The zero-valent nickel catalysts preferably is prepared prior to use. Methods of preparing the catalysts are disclosed in U.S. Pat. Nos. 3,152,158, 3,903,120, 3,328,443 and 3,496,215. However, catalysts can also be prepared in situ by placing in the reaction mixture an alkyl or aryl phosphite together with an intermediate zero-valent nickel compound or an intermediate organonickel compound having a nickel-carbon bond.

The intermediate zero-valent nickel compounds which form active catalyst in situ on addition of an alkyl or aryl phosphite can themselves be prepared in situ prior to addition of the phosphite ester. The intermediate zero-valent nickel compounds and also the zero-valent nickel catalysts and catalytic reaction products prepared in situ are characterized by having neutral ligands which are thought to be bonded to the central metal atom by both sigma- and pi-type bonds. This type of bonding is described, for example, in Cotton and Wilkinson (Advanced Inorganic Chemistry, Interscience Publishers, 1962, pp. 602–606).

The amount of catalyst can vary over a wide range, e.g., from a molar ratio of 2-methyl-3-butenenitrile to catalyst of 1:2 to 2000:1.

Butadiene may be introduced into the reaction in any form which is compatible with the reactants, e.g., as a vapor or a liquid, either singly or mixed with one or more of the reactants. Preferably at least 0.05% by weight based upon the weight of the reactants of butadiene is added to the reaction and preferably from 0.5–3% by weight is employed.

On an industrial scale, the 2-methyl-3-butenenitrile, catalyst and butadiene would be added continuously to a reaction vessel which would be heated to a temperature high enough for reaction following which the reaction products would be separated by known procedures to remove undesired and unreacted materials, to recover catalyst and to isolate a relatively pure linear 3-pentenenitrile stream.

The following examples are presented to illustrate but not to restrict the present invention. Parts and percentages are by weight unless otherwise noted.

EXAMPLES 1–3

A catalyst solution prepared following the general description of Example 1 of U.S. Pat. No. 3,903,120 to give a solution having the following analysis.

| | |
|---|---|
| 7% | linear pentenenitriles |
| 2.8% | 2-methyl-2-butenenitrile |
| 9.4% | dinitriles |
| 72% | tritolyl phosphite |
| 0.8% | zero-valent nickel |

Approximately 9 ml of this catalyst solution was combined with 25 ml of a distilled nitrile solution which had the approximate analysis:

| | |
|---|---|
| 92% | 2-methyl-3-butenenitrile |
| 4% | linear pentenenitriles |
| 3% | 2-methyl-2-butenenitrile |

The combined solutions had the following analysis:

| | |
|---|---|
| 62.5% | 2-methyl-3-butenenitrile (2M3BN) |
| 5% | linear pentenenitriles (PN) |
| 2.5% | 2-methyl-2-butenenitrile (2M2BN) |
| 3% | dinitriles (DN) |
| 23% | tritolylphosphite |
| 0.26% | zero-valent nickel |

The above solution was divided into four equal portions. Three of the portions were chilled in an ice bath and butadiene was introduced into the liquid therein with a gas syringe. The concentration of butadiene was determined by the weight increase of the portion. Approximately 0.75 ml of each portion was placed in a 7 ml glass lined sealed vessel and blanketed with nitrogen. The vessel and contents were heated from room temperature to 195° C. at a rate of 6° C./min following which the sample was cooled at the same rate to room temperature. This procedure was repeated for each 0.75 ml of each portion until approximately 2 ml of product of each portion were obtained and analyzed. The results are reported in Table 1.

TABLE 1

| Example No. | 1 | 2 | 3 | Comparison |
|---|---|---|---|---|
| Butadiene added (%) | .13 | .59 | 3.1 | 0 |
| Conversion of 2-methyl-3-butenenitrile (%) | 68 | 75 | 79 | 65 |
| Yield to linear pentenenitriles (%) | 98 | 99 | 99 | 96 |
| Yield to non-linear pentenenitriles and non-linear dinitrile (%) | 2.4 | 1.1 | 0.8 | 3.8 |
| Catalyst Utility $\frac{\text{Moles of linear PN produced}}{\text{Moles of nickel consumed}}$ | 135 | 190 | 240 | 130 |

EXAMPLES 4–6

Approximately 25 ml of a purified nitrile solution and 10 ml of a catalyst solution prepared following the general description of Example 1 of U.S. Pat. No. 3,903,120 were combined. Analyses showed the following approximate concentration:

| | |
|---|---|
| 59% | 2-methyl-3-butenenitrile |
| 6% | linear pentenenitriles |
| 1.4% | 2-methyl-2-butenenitrile |
| 2% | dinitriles |
| 24% | tritolylphosphite |
| 0.35% | zero-valent nickel |

This solution was divided into two portions. To one portion, butadiene was weighed in to give a 0.6% solution of butadiene. No butadiene was added to the second portion which served as a comparison. 2 ml samples of each solution were heated in a glass lined sealed vessel at 150° C. for one hour. The materials were rapidly cooled to quench the reaction and the products were analyzed. The same comparative procedure was repeated with reaction times of 2 hours and 6 hours. The results obtained are summarized in Table 2.

TABLE 2

| Reaction Time (Hrs) | 1 | | 2 | | 6 | |
|---|---|---|---|---|---|---|
| Example No. | 4 | Comparison | 5 | Comparison | 6 | Comparison |
| Butadiene Added (%) | .6 | 0 | .6 | 0 | .6 | 0 |
| 2M3BN Conversion (%) | 64 | 64 | 86 | 85 | 89 | 89 |
| Yield to linear pentenenitriles (%) | 99 | 97 | 99 | 98 | 98 | 95 |
| Yield to non-linear pentenenitriles and non-linear dinitriles (%) | 1.2 | 2.9 | 0.8 | 2.5 | 1.0 | 2.8 |
| Catalyst Utility | | | | | | |
| Moles of linear PN produced / Moles of nickel consumed | 1000 | 1000 | >1000 | 550 | >1500 | 500 |

What is claimed is:

1. In a process for the isomerization of 2-methyl-3-butenenitrile to linear pentenenitriles in the presence of a catalyst comprising a zero-valent nickel complexed with an organophosphorus compound, the improvement which comprises conducting said isomerization in the presence of at least 0.05% by weight based upon the weight of the reactants of butadiene.

2. The process of claim 1 wherein the amount of butadiene is 0.5–3%.

3. The process of claim 2 wherein butadiene is added to the isomerization.

* * * * *